United States Patent
Konakanchi et al.

(10) Patent No.: US 10,040,778 B2
(45) Date of Patent: Aug. 7, 2018

(54) ANHYDROUS LENALIDOMIDE FORM-I

(71) Applicant: Natco Pharma Limited, Hyderabad (IN)

(72) Inventors: Durga Prasad Konakanchi, Hyderabad (IN); Buchappa Gongalla, Hyderabad (IN); Kotayya Babu Sikha, Hyderabad (IN); Chandrasekar Kandaswamy, Hyderabad (IN); Kali Satya Bhujanga Rao Adibhatla, Hyderabad (IN); Venkaiah Chowdary Nannapaneni, Hyderabad (IN)

(73) Assignee: NATCO PHARMA LIMITED (IN)

( * ) Notice: Subject to any disclaimer, the term of this patent is extended or adjusted under 35 U.S.C. 154(b) by 0 days.

(21) Appl. No.: 14/794,275

(22) Filed: Jul. 8, 2015

(65) Prior Publication Data

US 2015/0353525 A1    Dec. 10, 2015

Related U.S. Application Data

(63) Continuation of application No. 14/151,519, filed on Jan. 9, 2014, now Pat. No. 9,108,945, which is a continuation of application No. 13/581,872, filed as application No. PCT/IN2010/000128 on Mar. 8, 2010, now Pat. No. 8,877,932.

(51) Int. Cl.
    *C07D 401/04*    (2006.01)
(52) U.S. Cl.
    CPC .................. *C07D 401/04* (2013.01)
(58) Field of Classification Search
    CPC ..................................... C07D 401/04
    USPC ......................... 514/323; 546/200
    See application file for complete search history.

(56) References Cited

U.S. PATENT DOCUMENTS

| | | | |
|---|---|---|---|
| 7,465,800 B2 * | 12/2008 | Jaworsky | C07D 401/04 546/200 |
| 8,877,932 B2 | 11/2014 | Konakanchi et al. | |
| 8,946,265 B2 * | 2/2015 | Gore | C07D 401/04 514/323 |
| 9,108,945 B2 | 8/2015 | Konakanchi et al. | |
| 2005/0096351 A1 | 5/2005 | Jaworsky et al. | |
| 2013/0059889 A1 | 3/2013 | Konakanchi et al. | |

FOREIGN PATENT DOCUMENTS

| | | |
|---|---|---|
| CN | 101580501 B | 3/2011 |
| IN | 47/CHE/2006 A | 11/2007 |
| WO | 2005/23192 A2 | 3/2005 |
| WO | 2009/114601 A2 | 9/2009 |
| WO | 2010/100476 A2 | 9/2010 |
| WO | 2010139266 A1 | 9/2010 |

OTHER PUBLICATIONS

Bernstein "Polymorphism in molecular crystals" p. 115-119 (2002).*
Byrn "Solid state chemistry of drugs" p. 63 (1999).*
Davidovich et al. "Detection of polymorphism . . . " Am. Phar. Rev. 7(1) 10, 12, 14, 15, 100 (2004).*
Dean "Analytical chemistry handbook" p. 10.24-10.26 (1995).*
Celegen "Revlimid capsule" product information p. 1-26 (2009).*
Yin et al. "Selecting and controlling . . . " Current Opin. Drug discovery & Develop. 11(6) 771-777 (2008).*
International Search Report, dated Nov. 19, 2010, PCT application No. PCT/IN2010/00128, 4 pages.
Anonymous Third Party Observation in corresponding European Publication No. EP 2545043 submitted to the EPO Sep. 5, 2013; 10 pages.
Brittain et al., "Polymorphism in Pharmaceutical Solids passage," Polymorphism in Pharmaceutical Solids, 1999, pp. 235-238.
Brittain et al., "X-ray Diffraction III: Pharmaceutical Applications of X-ray Powder Diffraction," Spectroscopy, 2001, vol. 16, pp. 142-150.
Comparison of XRPD Data filed by an Anonymous Third Party in corresponding European Publication No. EP 2545043 submitted to the EPO Sep. 5, 2013; 5 pages.
Manish, Maheshwari, et al., "Melt sonocrystallization of ibuprofen: Effect on crystal properties," *European Journal of Pharmaceutical Sciences* (2005) 25:41-48.
Natco Pharma Limited ; "Lenalid* 5," Lenalidomide Capsules 5mg; product marketed in India in 2007; see, photocopy of product packaging and insert.
941 Characterization of Crystalline and Partially Crystalline Solids by X-Ray Powder Diffraction (XRPD). *The United States Pharmacopeial Convention* (2014) 503-509.
2.9.33. Characterisation of Crystalline and Partially Crystalline Solids by X-Ray Powder Diffraction (XRPD). *European Pharmacopoeia 8.0* (Jan. 2009:20933) 339-343.
2.58 X-Ray Powder Diffraction Method. *Japanese Pharmacopoeia.* 75-79.
Third Party Observation dated May 19, 2016 for EP 20100725291 filed Jan. 16, 2013, 15 pages.

* cited by examiner

*Primary Examiner* — Patricia L Morris
(74) *Attorney, Agent, or Firm* — Mintz Levin Cohn Ferris Glovsky and Popeo PC (57) ABSTRACT

Anhydrous polymorphic form-I of anti cancer drug, Lenalidomide whose chemical name is 3-(4-amino-1-oxo-1,3-dihydro-isoindole-2-yl)-piperidine-2,6-dione, is disclosed. Alternate methods for making anhydrous polymorphic form-I of Lenalidomide are also disclosed.

8 Claims, 8 Drawing Sheets

| Angle 2-Theta ° | d value Angstrom | Intensity % % |
|---|---|---|
| 7.879 | 11.21187 | 31.9 |
| 10.175 | 8.68633 | 14.9 |
| 11.269 | 7.84565 | 13.2 |
| 14.327 | 6.17721 | 71.0 |
| 14.825 | 5.97072 | 6.2 |
| 15.772 | 5.61449 | 20.3 |
| 16.277 | 5.44134 | 14.2 |
| 17.646 | 5.02198 | 27.3 |
| 20.099 | 4.41442 | 24.9 |
| 20.508 | 4.32723 | 100.0 |
| 22.703 | 3.91356 | 4.5 |
| 23.728 | 3.74678 | 41.9 |
| 24.098 | 3.69015 | 41.6 |
| 24.796 | 3.58779 | 7.9 |
| 25.230 | 3.52703 | 11.6 |
| 25.987 | 3.42594 | 31.9 |
| 28.320 | 3.14885 | 19.0 |
| 28.936 | 3.08320 | 4.5 |
| 31.338 | 2.85215 | 6.0 |
| 31.901 | 2.80303 | 4.3 |
| 32.595 | 2.74494 | 20.3 |
| 33.516 | 2.67156 | 9.7 |
| 38.133 | 2.35805 | 3.9 |

| Angle 2-Theta ° | d value Angstrom | Intensity % |
|---|---|---|
| 7.588 | 11.64182 | 9.0 |
| 7.857 | 11.24333 | 6.9 |
| 11.259 | 7.85276 | 10.1 |
| 11.982 | 7.38060 | 100.0 |
| 13.106 | 6.74978 | 23.1 |
| 13.804 | 6.40987 | 24.9 |
| 14.030 | 6.30724 | 20.5 |
| 15.210 | 5.82042 | 11.1 |
| 15.704 | 5.63854 | 39.4 |
| 16.414 | 5.39620 | 13.0 |
| 17.122 | 5.17450 | 11.4 |
| 18.009 | 4.92179 | 19.6 |
| 18.403 | 4.81715 | 5.6 |
| 19.068 | 4.65060 | 23.9 |
| 19.483 | 4.55257 | 15.8 |
| 20.633 | 4.30119 | 16.1 |
| 21.351 | 4.15818 | 9.1 |
| 22.044 | 4.02904 | 51.4 |
| 22.514 | 3.94598 | 35.4 |
| 23.042 | 3.85680 | 7.2 |
| 23.822 | 3.73216 | 29.5 |
| 24.419 | 3.64228 | 9.2 |
| 25.467 | 3.49469 | 3.8 |
| 26.181 | 3.40103 | 10.5 |
| 26.587 | 3.35002 | 31.3 |
| 27.567 | 3.23307 | 20.6 |
| 29.194 | 3.05656 | 21.3 |
| 31.112 | 2.87229 | 11.7 |
| 31.988 | 2.79567 | 8.5 |
| 33.154 | 2.69993 | 7.5 |
| 33.867 | 2.64471 | 7.9 |
| 34.459 | 2.60064 | 6.3 |
| 35.087 | 2.55550 | 5.6 |
| 35.602 | 2.51972 | 3.4 |
| 37.789 | 2.37874 | 6.4 |
| 41.420 | 2.17822 | 3.4 |
| 43.071 | 2.09845 | 5.2 |
| 45.937 | 1.97398 | 5.2 |

Fig. 6

ANHYDROUS LENALIDOMIDE FORM-I

The present invention relates to anhydrous polymorphic form-I of Lenalidomide, whose chemical name is 3-(4-amino-1-oxo-1,3-dihydro-isoindole-2-yl)-piperidine-2,6-dione. Lenalidomide is an anti cancer drug useful in the treatment of myelodysplastic syndrome. The invention also relates to alternate processes for the preparation of anhydrous polymorphic form-I of Lenalidomide.

PRIOR ART

Various polymorphic forms of 3-(4-amino-1-oxo-1,3-dihydro-isoindole-2-yl)-piperidine-2,6-dione (also called by its generic name—Lenalidomide) are reported in patent application US 2005/0096351 A1. In this patent invention, various polymorphic forms such as Form-A, Form-B, Form-C, Form-D, Form-E, Form-F, Form-G and Form-H have been reported. The representative figure of powder X-ray diaffractograms, DSC, TGA thermographs and UV-visible spectra of all these polymorphic Form-A to Form-H are mentioned in this patent application. It is also reported in this patent application that the polymorphic Form-A is anhydrous form and no moisture content given. Polymorphic form-B is hemi hydrate with moisture content of 3.1%. Polymorphic Form-C is a hemi-solvate of acetone and form-D is solvated with water and acetonitrile. Form-E is a dihydrate with a moisture content of 11.9%. Form-F is an unsolvated material and is obtained by complete dehydration of Form-E material. Form-G is also an unsolvated and is obtained by slurrying Form-B and Form-E in tetrahydrofuran solvent. The water contents for Form-F and G are not given in the description and examples. Form-H is a crystalline solid hydrated with above 0.25 moles of water.

Form-A:

The processes for making these polymorphic forms are also given in the patent description very briefly. The temperature condition for the preparation of anhydrous Form-A is given in a table-I of the above-mentioned patent, heating Lenalidomide at 175° C. for 1 hour. Interconversion studies show that Form-B typically converts to Form-A in a tetrahydrofuran solvent system. De-solvation experiments show that upon heating at 175° C. for about 5 min, Form-B typically converts to Form-A. It is also mentioned that Form A was obtained by crystallization from various non-aqueous solvents including 1-butanol, butyl acetate, ethanol, ethyl acetate, methanol, methyl ethyl ketone, and tetrahydrofuran. Form A is a crystalline, unsolvated solid that melts at approximately 270.degree. C. Also given in the patent text that Form A is not hygroscopic and appears to be the most thermodynamically stable anhydrous polymorph of 3-(4-amino-1-oxo-1,3-dihydro-isoindol-2-yl)-piperidine-2,6-Dione.

Form-B:

Form B, the hemihydrate, was also obtained by crystallization from the solvents hexane, toluene and water. It is mentioned in the patent description that Lenalidomide Form-B is the desired polymorphic form for active pharmaceutical ingredient (API) and this form has been used in the formulation of API into drug product for clinical studies.

Amorphous polymorphic form of 3-(4-amino-1-oxo-1,3-dihydro-isoindole-2-yl)-piperidine-2,6-dione and Lenalidomide methane sulfonic acid salt are reported and claimed in patent application WO 2009/114601 A2. The representative figure of powder X-ray diaffractograms, DSC and TGA thermographs of amorphous polymorphic Form is mentioned in this patent application. In the examples 3 and 4 process for making Lenalidomide and their powder X-ray diaffractograms are given (FIGS. 7 and 8) but not claimed.

Acid addition salts and their polymorphic forms of 3-(4-amino-1-oxo-1,3-dihydro-isoindole-2-yl)-piperidine-2,6-dione are reported and claimed in patent application WO 2009/111948 A1. The representative figures of powder X-ray diaffractograms and IR spectra are given.

PRESENT INVENTION

In search of finding for new polymorphs of Lenalidomide, we surprisingly found an stable anhydrous form, which is obtained by distilling partially or completely the solvents dimethylformamide, isopropyl alcohol or acetonitrile solvents containing Lenalidomide or its hydrated forms under normal atmospheric pressure or at reduced pressures and also by azeotropic distillation in toluene and other suitable solvents. The thus obtained anhydrous novel form is very stable at room temperature (25-35° C.) and is not absorbing water or converting to any reported hydrated forms. After storage for more than a year at room temperature (25-35° C.) the anhydrous form is not converted into any hydrated from such as Form-B (hemihydrate) or Form-E. The moisture content in the azeotropically distilled material is always less than 0.1%.

The anhydrous polymorphic form of Lenalidomide, hereinafter called as Form-I, is obtained, after the completion of the catalytic reduction of nitro group of 3-(4-nitro-1-oxo-1,3 dihydro-isoindol-2-yl)-piperidine-2,6-dione and then filteration of the catalyst followed by removal of solvent dimethyl formamide, under vacuum. The Form-I can also be obtained by suspending the wet Lenalidomide cake, which is obtained directly after filtration of the catalyst from the reaction mass, in solvents such as isopropyl alcohol, dimethyl formamide and acetonitrile followed by reducing or completely distilling the solvents at temperatures varying 65° C. to 110° C. under vacuum or without vacuum and then finally drying at temperature varying from 40-110° C. either under vacuum or without vacuum. Also the anhydrous polymorphic form-I of Lenalidomide is obtained by filteration and drying at temperature varying from 40-110° C. either under vacuum or with out vacuum after azeotropically distilling the solvent toluene completely or partially with or without vacuum, at temperatures varying 65° C. to 110° C.

The polymorphic Form-I prepared by above mentioned methods are having identical p-XRD, IR, TGA and DSC pattern.

Yet another invention of this patent application is the preparation of the hemihydrate form of Lenalidomide (Form-B as per US 2005/0096351 A1) by an alternate method. In the patent US 2005/0096351 A1, the preferred process parameters have been identified and given as 1.

1. Hot slurry temperature of 70-75° C.
2. Product filtration of 3-(4-amino-1-oxo-1,3 dihydro-isoindol-2-yl)-piperidine-2,6dione at 65-75° C.
3. Drying under vacuum at 60-70° C. is preferred for an efficient removal of unbound water in 3-(4-amino-1-oxo-1,3 dihydro-isoindol-2-yl)-piperidine-2,6dione wet cake.
4. The filtration step of 3-(4-amino-1-oxo-1,3dihydro-isoindol-2-yl)-piperidine-2,6dione may be a time sensitive operation. The use of efficient solid-liquid separation equipment is preferred.
5. Holding periods of water-wet cake of 3-(4-amino-1-oxo-1,3-dihydro-isoindol-2-yl)-piperidine-2,6dione at KF higher than 5% may cause the kinetic equilibrations of polymorph B to mixed polymorphs of E and B.

Optimum conditions were determined to be 10 volumes of solvent (H₂O), 70-80° C. for 6-24 hours.

Whereas in the present process, the crude Lenalidomide solid obtained after transfer hydrogenation or catalytic hydrogenation of 3-(4-nitro-1-oxo-1,3 dihydro-isoindol-2-yl)-piperidine-2,6-dione is completely freed from the solvents such as dimethylformamide to obtain polymorphic form-I or alternatively after distillation of the solvent from the reaction mixture then the residue is reacted with molar equivalent of dilute hydrochloric acid and dissolved in water. Activated carbon is added to the solution and filtered through hyflo bed. The clear filtered solution is neutralised and adjusted the pH to 7.5 to 8.0 with a suitable base such as ammonia solution or aqueous solutions of hydroxides, carbonates or bicarbonates of sodium, potassium or ammonium to get the Lenalidomide precipitated. The filtered product is washed plenty of water to remove the inorganics, followed by drying under vacuum at temp 65° C. to 110° C. This is a very simple, reproducible and commercially feasible process for making Lenalidomide Form-B. The IR, PXRD, TGA DSC of the thus obtained product are identical with the product obtained by following the optimized process given in the patent US 2005/0096351.

BRIEF DESCRIPTION OF THE DRAWINGS

Specific aspects of the invention can be understood with reference to the attached figures.

The synthetic process for Lenalidomide starts from side chain bromination of 2-methyl-3-nitro-benzoate with N-bromosuccinimide in a suitable solvents such as chloroform, ethylene dichloride, carbon tetrachloride, chlorobenzene, 1,2-dichlorobenzene or mixture of these solvents at temperature in the range of 60° C. to 135° C. to obtain 2-bromomethyl-3-nitro-benzoate.

The 3-(4-nitro-1-oxo-1,3 dihydro-isoindol-2-yl)-piperidine-2,6-dione solid is obtained by alkylation followed by cyclisation of methyl 2-bromomethyl-3-nitro-benzoate with d, 1-3-Aminoglutarimide in solvents such as dimethylformamide, methanol, ethanol, acetonitrile and mixture of these solvents. The thus obtained 3-(4-nitro-1-oxo-1,3 dihydro-isoindol-2-yl)-piperidine-2,6-dione has HPLC purity of above 99.0% and is taken for the next stage without further purification.

By catalytic hydrogenation of 3-(4-nitro-1-oxo-1,3 dihydro-isoindol-2-yl)-piperidine-2,6-dione in solvents such as dimethylformamide, methanol, ethanol, isopropyl alcohol or mixture of these solvents at temperature 50-100.0° C. under pressure or bubbling of hydrogen gas at atmospheric pressure, then filteration of the catalyst followed by distillation under high vacuum Lenalidomide polymorphic form-I is obtained. The polymorphic form-I of Lenalidomide can also be obtained by transfer hydrogenation of 3-(4-nitro-1-oxo-1,3 dihydro-isoindol-2-yl)-piperidine-2,6-dione using solvents dimethylformamide, methanol, ethanol, isopropyl alcohol or mixture of these solvents at temperature 50-100.0° C. using ammonium formate or formic acid as source of hydrogen. The precious metal catalysts used in the hydrogenation are Raney Nickel, palladium etc., followed by filteration of catalyst and distillation of the solvent under high vacuum.

The purity of anhydrous polymorphic Form-I of Lenalidomide obtained by purification from acid base treatment followed by distillation in the solvents such as isopropyl alcohol or acetonitrile solvents is more than 99.90% with any single impurity level by not exceeding 0.10%. The moisture content is always less than 0.1%. The anhydrous polymorphic Form-I of Lenalidomide is charecterised by 1H NMR, 13C NMR and Mass spectra.

The Powder XRD 2θ° values of the anhydrous Form-A of Lenalidomide reported in the patent application US 2005/0096351 A1 are compared with the Powder XRD 2θ° values of polymorphic Form-I reported in the present invention and differences are tabulated in the following table-I

TABLE I

Comparision of 2θ° values between Form-A and Form-I of the present invention

| S. NO. | 2θ° Values of Form-I of present invention | 2θ° Values of patent (Form-A) Sample |
| --- | --- | --- |
| 01 | 7.793 (Single peak) | About 8 (Two significant peaks) |
| 02 | 10.120 | |
| 03 | 11.201 | |
| 04 | 14.285 | |
| 05 | 14.766 | 14.5 |
| 06 | 15.716 | |
| 07 | 16.173 | 16.0 |
| 08 | 17.586 | 17.5 |
| 09 | 18.375 | |
| 10 | 20.030 | |
| 11 | 20.493 | 20.5 |
| 12 | 22.648 | |
| 13 | 23.660 | |
| 14 | 24.029 | 24.0 |
| 15 | 24.747 | |
| 16 | 25.187 | |
| 17 | 25.910 | 26.0 |
| 18 | 28.261 | |
| 19 | 32.521 | |
| 20 | 33.485 | |
| 21 | 34.858 | |
| 22 | 43.170 | |

DETAILED DESCRIPTION FOR THE PREPARATION OF LENALIDOMIDE FORM-I

The anhydrous polymorphic Form-I of Lenalidomide can also be prepared by taking the hydrated Form-B or Form-E of Lenalidomide in a solvent such as isopropyl alcohol or in acetonitrile and the temperature is increased to refluxing. After maintaining for about one hour the solvent is partially distilled under atmospheric pressure. Moisture content is checked for the distilled solvent and if expected amount of water in the reaction mass is completely removed the reaction mass is cooled and the product is filetered. If necessary further solvent can be removed by partial distillation to expel the water in the product. Alternatively the solvent is completely distilled off from the vessel either by atmospheric distillation or under vacuum and upon cooling a co-solvent such as hexane, heptane, cyclohexane, toluene or ethyl acetate is added to the residue and the product is slurried and filtered.

The polymorphic Form-I of Lenalidomide can also be prepared by taking the hydrated form of Lenalidomide in a solvent such as toluene, xylene or cyclohexane and the water in the product is completely separated by azeotropic distillation. After water removal by azeotropic distillation, the reaction mass is cooled and the product is filetered. Alternatively the solvent is completely distilled off from the vessel either by atmospheric distillation or under vacuum and upon cooling a co solvent such as hexane, heptane, isopropyl alcohol or ethyl acetate are added to the residue and the product is slurried and filtered.

The filtered wet product is dried at a temperature varying from 40-110° C. either under vacuum or with out vacuum till the residual solvents are under specified limits.

Figure 1A:
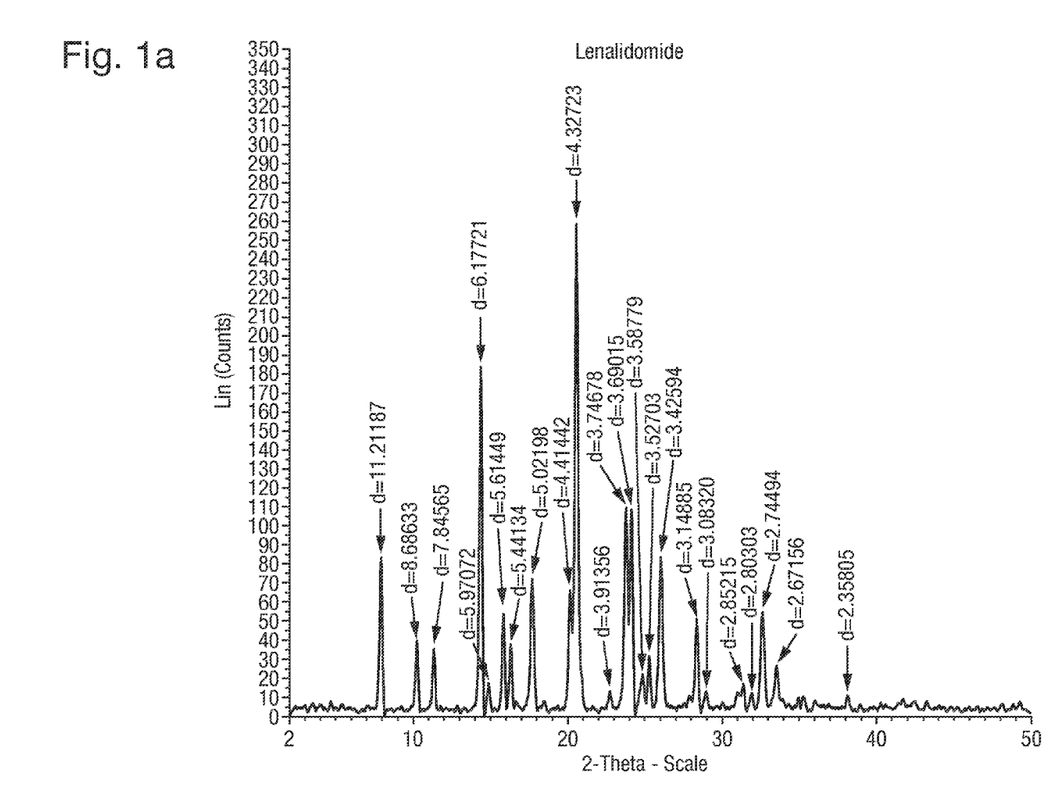
FIGS. 1a and 1b provide a representative powder X-ray diffraction (PXRD) pattern of Lenalidomide anhydrous Form-I, prepared by example-5.
Figure 1B:
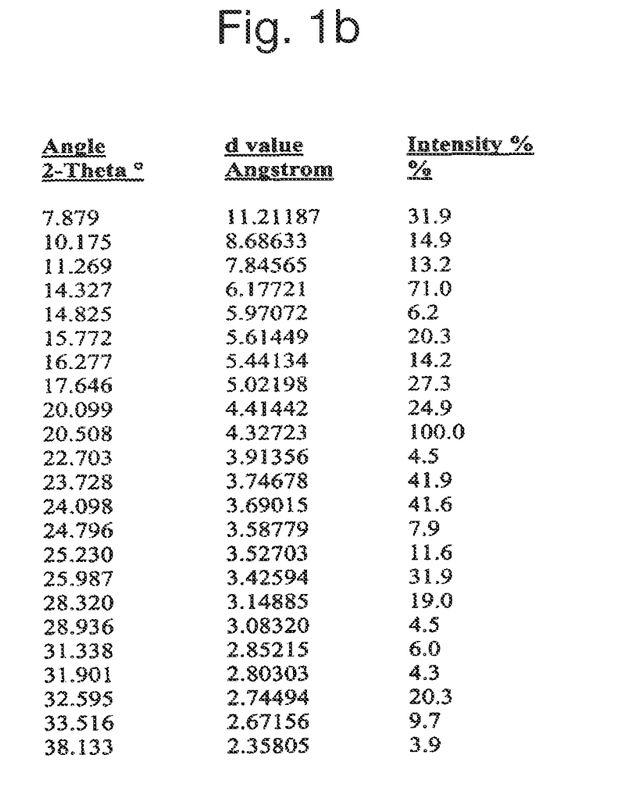

FIG. 1 shows a representative P-XRD pattern of Form-I. The pattern is characterized by peaks, preferably significant peaks, at (2θ) 7.793 (distinct single peak), 10.120, 11.201, 14.285, 14.766, 15.716, 16.173, 17.586, 18.375, 20.030, 20.493, 22.648, 23.660, 24.029, 24.747, 25.187, 25.910, 28.261, 32.521, 33.485, 34.858, 43.170.

Figure 2:
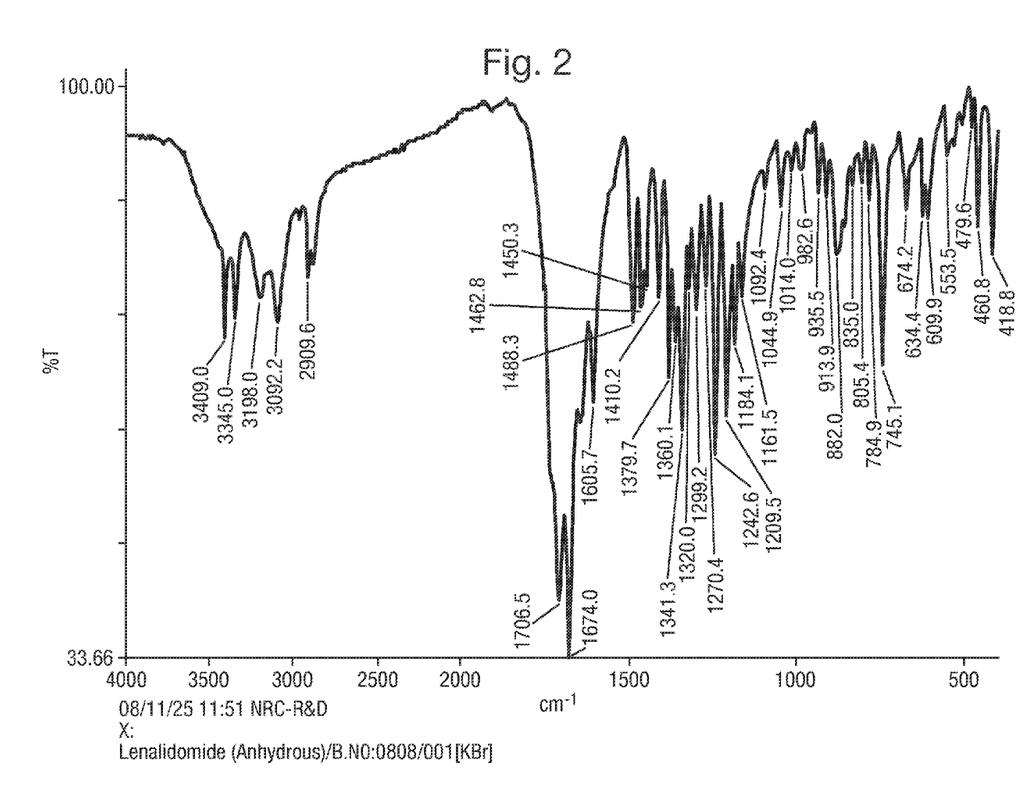
FIG. 2 provides a representative IR spectrum of Lenalidomide anhydrous Form-I.
Figure 3:
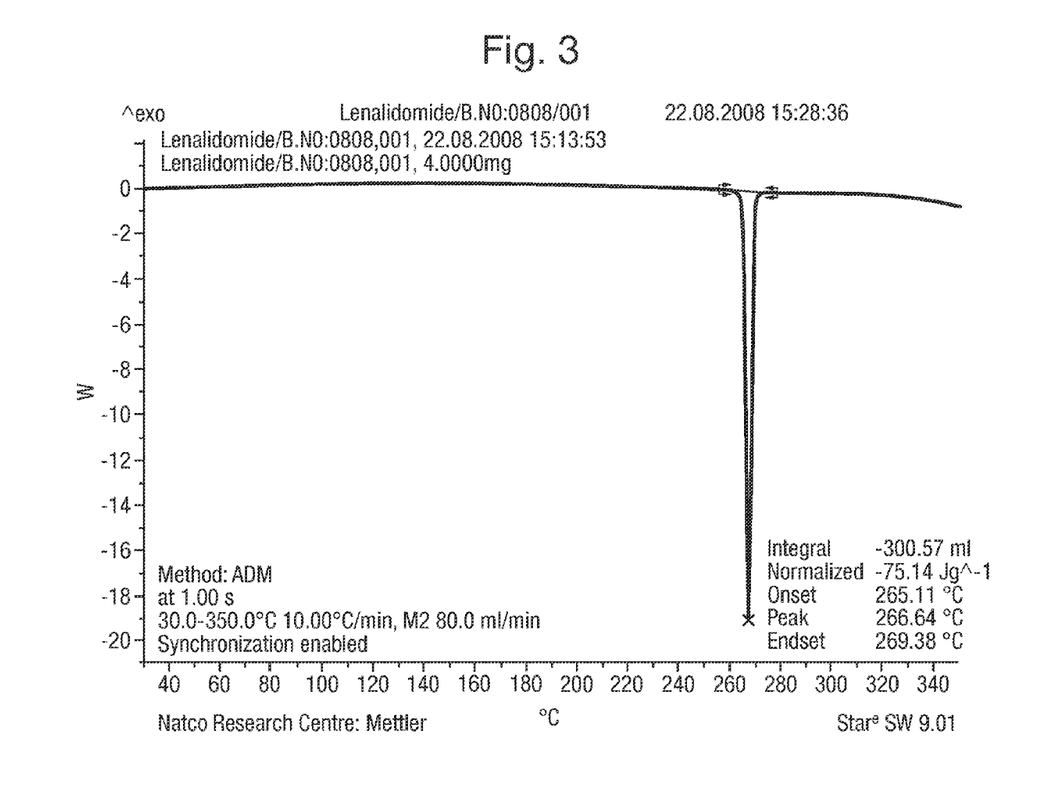
FIG. 3 provides a representative thermo gravimetric analysis (TGA) of Lenalidomide anhydrous Form-I.
Figure 4:
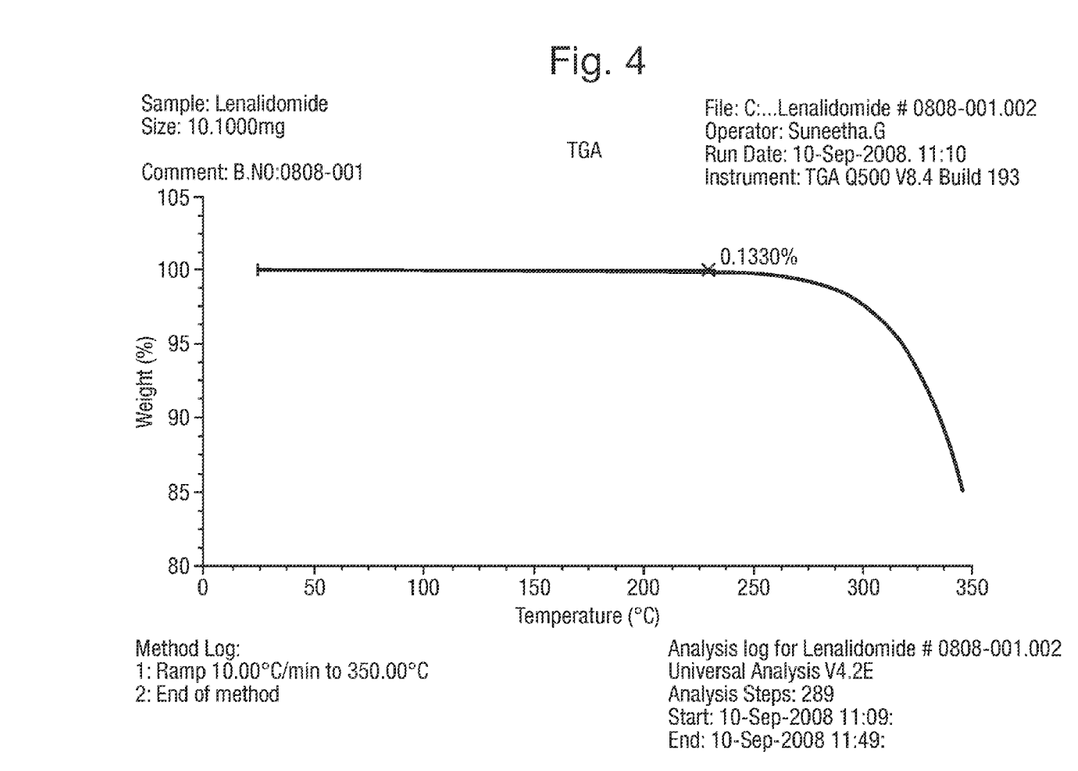
FIG. 4 provides a representative differential scanning calorimeter (DSC) thermogram of Lenalidomide anhydrous Form-I.
Figure 5A:
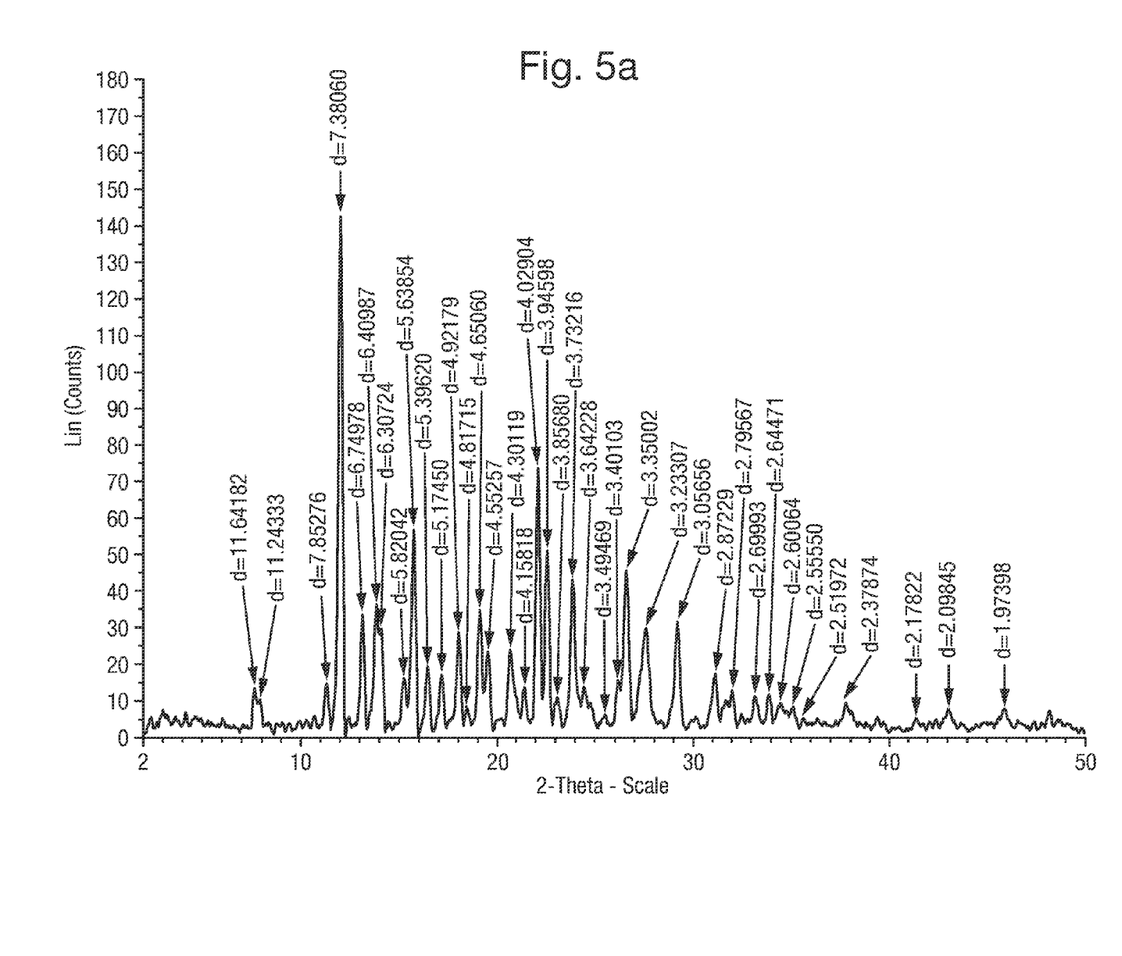
FIGS. 5a and 5b provide a representative X-ray powder diffraction (XRPD) pattern of Form-B, which is prepared by example-4.
Figure 5B:
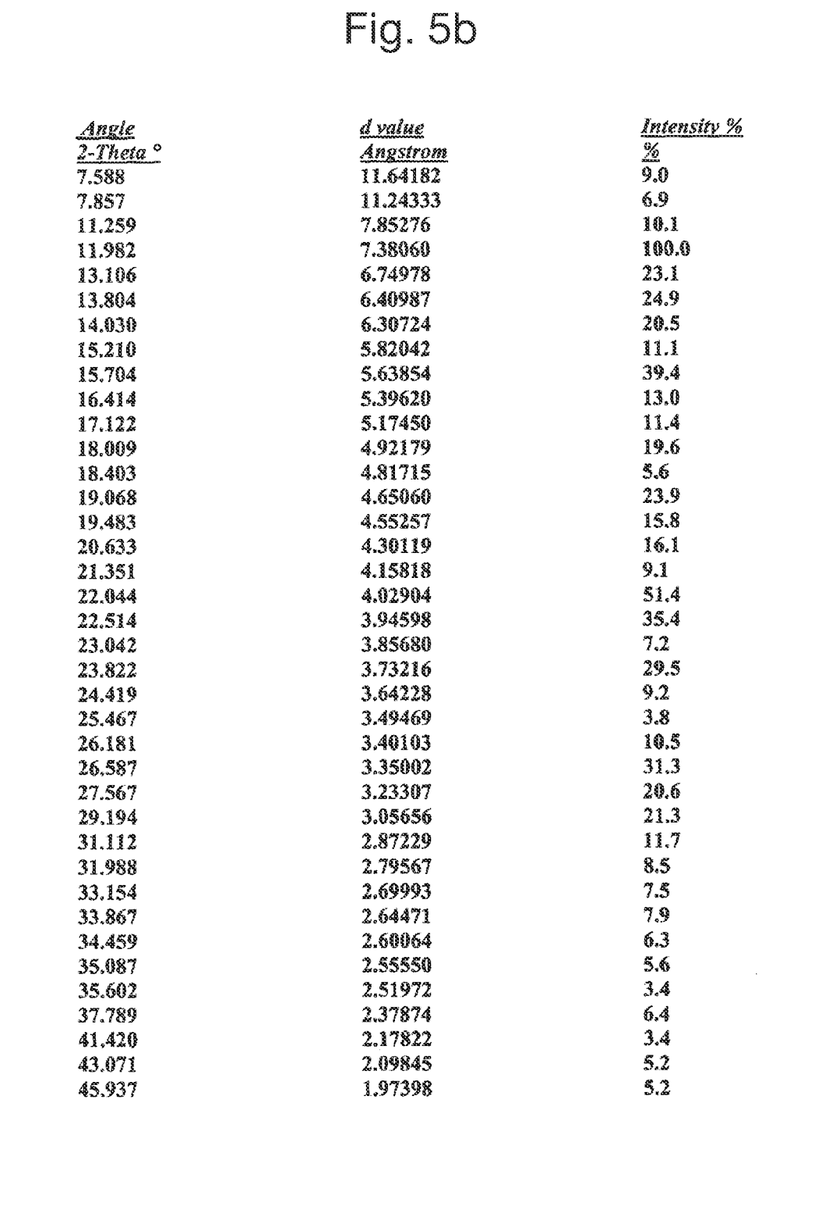
Figure 6:
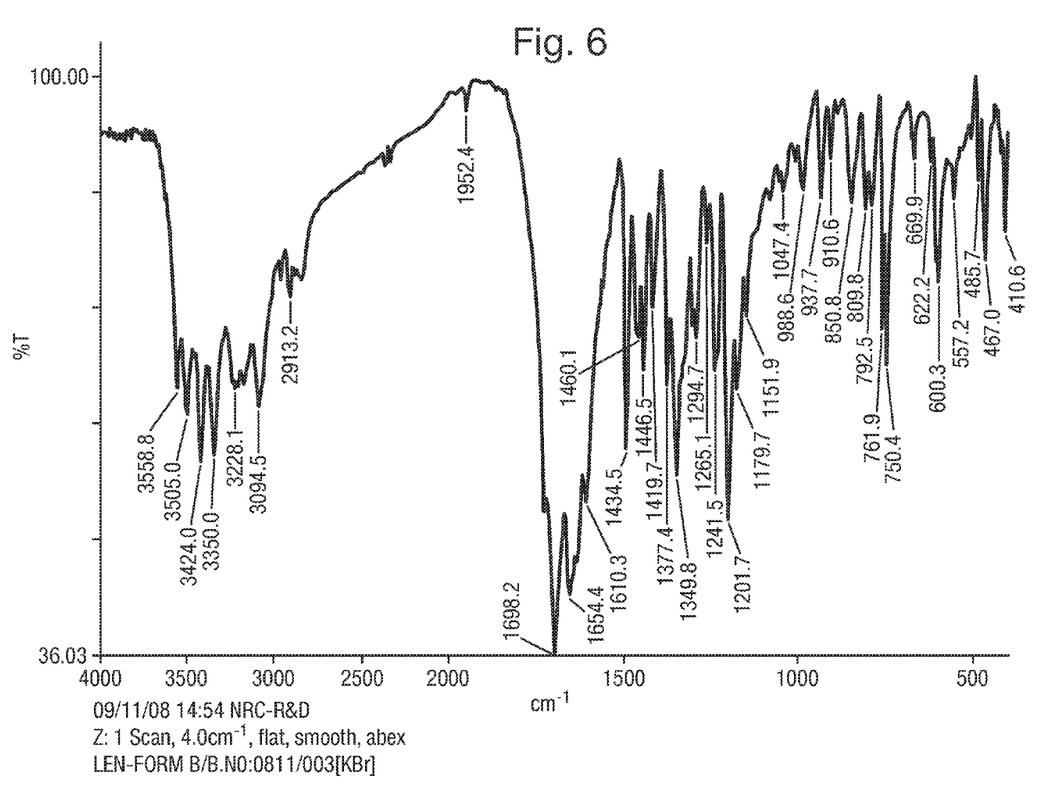
FIG. 6 provides a representative IR spectrum of Form-B, which is prepared by example-4.

Representative IR spectra, DSC thermograph and TGA thermographs are provided in FIGS. 2, 3 and 4 respectively.

Representative thermal characteristics of Form polymorphic Form-I are shown in FIG. 2.

The DSC curve of Form A exhibits an endotherm at about 270° C.

TGA data show no weight loss up to about 150° C., indicating an unsolvated or anhydrous material. Weight loss above 150° C. is attributed to decomposition.

The moisture content of the Form-I samples prepared is always less than 0.1% Form B The hemihydrate form of Lenalidomide (reported as polymorphic Form-B as per patent application US 2005/0096351 A1) is also prepared by an alternate method. The crude Lenalidomide solid obtained after hydrogenation of 3-(4-nitro-1-oxo-1,3 dihydro-isoindol-2-yl)-piperidine-2,6-dione is reacted with dilute hydrochloric acid and dissolved in water. Activated carbon is added and filtered through hyflo bed. The clear filtered solution is neutralised and adjusted the pH to 7.5 to 8.0 with a suitable base such as ammonia solution or solutions of hydroxides, carbonates or bicarbonates of sodium, potassium or ammonium to get the Lenalidomide precipitated. Filtered and washed the precipitate with plenty of water to remove the inorganics. Dried the wet product in a vacuum oven to obtain hemihydrate form of Lenalidomide with a HPLC purity of above 99.9%.

The hydrogenation step can be carried out by using Palladium or Raney Nickel as catalyst and can be carried out under hydrogen pressure in a hydrogenarator or by bubbling hydrogen gas in a conventional reactor at atmospheric pressure. And also the reduction of nitro group step can be also be carried out by transfer using Palladium as catalyst and formic acid or ammonium formate as source of hydrogen in a conventional reactor at atmospheric pressure. By using a conventional reactor in the transfer hydrogenation or in the catalytic hydrogenation with hydrogen gas bubbling at atmospheric pressure usage of speciality and expensive equipment such as pressure hydrogentator vessel can be avoided. After the hydrogenation is complete the catalyst is filtered and the clear filtered solution is neutralised and adjusted the pH to 7.5 to 8.0 with a suitable base such as ammonia solution or solutions of hydroxides, carbonates or bicarbonates of sodium, potassium or ammonium to get Lenalidomide precipitated. Filtered and washed the precipitate with plenty of water to remove the inorganics. Dried the wet product in a vacuum oven to obtain hemihydrate form of Lenalidomide with a HPLC purity of above 99.9%. The purification of Lenalidomide by acid base treatment is a very simple and inexpensive. This process is not reported in the literature and is a novel purification step in the synthesis of Lenalidomide. This process is feasible on a commercial scale.

The synthetic process for Lenalidomide starts form side chain bromination of 2-methyl-3-nitro-benzoate with N-bromosuccinimide in suitable solvents such as chloroform, ethylene dichloride, carbon tetrachloride, chlorobenzene, 1,2-dichlorobenzene or mixture of these solvents at temperature in the range of 60° C. to 135° C. to obtain 2-bromomethyl-3-nitro-benzoate. The product obtained is 2-bromomethyl-3-nitro-benzoate having a HPLC purity of over 99.0%.

The 3-(4-nitro-1-oxo-1,3 dihydro-isoindol-2-yl)-piperidine-2,6-dione solid is obtained by alkylation followed by cyclisation of methyl 2-bromomethyl-3-nitro-benzoate with (d, l)-3-aminoglutarimide in solvents such as dimethylformamide, methanol, ethanol, acetonitrile and mixture of these solvents. The thus obtained 3-(4-nitro-1-oxo-1,3 dihydro-isoindol-2-yl)-piperidine-2,6-dione is having HPLC purity of above 99.0% and is taken for the next stage with out further purification.

The crude Lenalidomide is obtained by catalytical hydrogenation of 3-(4-nitro-1-oxo-1,3 dihydro-isoindol-2-yl)-piperidine-2,6-dione in solvents such as dimethylformamide, methanol, ethanol, isopropyl alcohol or mixture of these solvents at temperature 50-100.0° C. under pressure or bubbling of hydrogen gas at atmospheric pressure. The crude Lenalidomide can also be obtained by transfer hydrogenation of 3-(4-nitro-1-oxo-1,3 dihydro-isoindol-2-yl)-piperidine-2,6-dione using solvents dimethylformamide, methanol, ethanol, isopropyl alcohol or mixture of these solvents at temperature 50-100.0° C. using ammonium formate or formic acid as source of hydrogen. The precious catalysts used in the hydrogenation are Raney Nickel, palladium etc., The purity of anhydrous polymorphic form of Lenalidomide obtained by purification from acid base treatment followed by distillation in the solvents such as isopropyl alcohol or acetonitrile solvents is more than 99.90% with any single impurity by not more than 0.10%. The moisture content is always less than 0.1%. The anhydrous polymorphic form of Lenalidomide is charecterised by 1H NMR, 13C NMR and Mass spectra.

We have compared the Powder XRD 2θ° values of the form-B samples of Lenalidomide prepared with that of the Powder XRD 2θ° values for the Form-B in the patent application US 2005/0096351 A1 and found that the both the values are exactly matching. The IR spectrum is also concordant with that of the reported. The TGA thermograph and the DSC spectrum are also comparable with that of sample prepared by this application procedure.

Thermal Stability of Lenalidomide Form I

The lenalidomide Form I obtained after drying temperature 65 to 75° C. under vacuum is taken subjected to heating at 95 to 105° C. in oil bath, kept in rotator vapor for 7 days, cool to room temperature and the sample is analyzed per IR, NMR, XRPD (X-ray powder diffractometry), DSC (differential scanning calorimetry) & TGA (thermogravimetry). No change is observed in spectral data. The moisture content is also determined for sample and found to be less than 1%. No further change in impurity profile is observed.

Representative thermal characteristics of Form A are shown in FIG.

TGA data show a small weight loss up to about 150° C., indicating an unsolvated material. Weight loss above 150° C. is attributed to decomposition On the basis of our work weight loss between 25° C. and 225° C. is 0.13%. The DSC curve of Form A exhibits an endotherm at about 266.64° C.

Accelerated Stability Studies

The lenalidomide Form I sample are subjected to accelerated stability studies under following conditions & analyzed at initial after 1, 2, 3 and 6 months.
Condition 1—temperature: 40° C.±2° C.
Relative humidity: 75% RH±5%
Condition 1—temperature: 30° C.±2° C.
Relative humidity: 65% RH±5%

We have not observed major deviation in quality of samples analysed of initial samples after 1, 2, 3 and 6 months.

The moisture content is marginally increased from 0.09% w/w to 0.21% w/w. No increase in impurity profile is observed in 1, 2, 3 and 6 months sample. So under the above stress condition the lenadomide Form I sample is not converted in any of the hydrated polymorphic form such hemi hydrated & dihydrate Form E.

Intrinsic Dissolution and Solubility Studies

Dissolution

Dissolution experiments were carried out in a ELECTRO-LAB-8 dissolution apparatus equipped with a ETC-112 temperature controller. An intrinsic dissolution apparatus (Woods apparatus) was used. Samples were compressed at 2.0 metric tons for 1 min in KBr hydraulic press, giving a sample surface of 0.50 cm$^2$. A dissolution medium consisting of 900 mL HCl buffer, pH 1.8, with 1% sodium lauryl sulfate, was used for each experiment. The medium was degassed by vacuum filtration through a 0.45-μm nylon filter disk and maintained at 37° C. The apparatus was rotated at 50 rpm for each experiment. Aliquots were filtered immediately using 0.45-μm nylon syringe filters. In some cases, the undissolved solids were recovered and analyzed by X-ray powder diffraction (XRPD).

Solubility

Equilibrium solubility experiments were conducted in a 100-mL, three-neck, round-bottom flask immersed in a constant temperature oil bath maintained at 25° C. A solid sample of 450 mg was stirred in 50 mL of dissolution medium (HCl buffer, pH 1.8, with 1% sodium lauryl sulfate) using a mechanical stir rod. Aliquots were filtered and centrifuged at 3500 rpm using 0.2-μm nylon syringe filters and immediately diluted 1 mL→50 mL, then 5 mL→25 mL with dissolution medium. In some cases, the undissolved solids were recovered and sent for X-ray powder diffraction (XPRD) studies.

Results:

Both the solubility and dissolution experiments were conducted in a medium of HCl buffer, pH 1.8, containing 1% sodium lauryl sulfate. The solubilities were estimated to be 3.15 mg/ml for Form I& 3.28 mg/ml for Form B, respectively. The dissolution rates of Forms-I& Form-B were estimated to be 421 mg/min/cm$^2$ & 0.250 mg/min/cm$^2$ respectively.

Whereas the solubilities of both the Form-I and Form-B are similar, there is a high dissolution rate can be seen in Form-I compared to Form-B Humidity Test The anhydrous form of lenalidomide along with two batches (0812/006 & 0812/007 &) were
subjected for humidity test.

Experimental

NaBr, NH4Cl, KOH, Na2HPO4 were used as Saturated solution at temperature 25.1° C., 25° C., 24.7° C., 26.8° C. and humidity 84%, 79%, 23%, 93% respectively at initial water content of 0.08%.

Result—

The water content after humidity test were 0.21% w/w, 0.13% w/w, 0.12% w/w, 0.10% w/w respectively.

Hence it is seen that humidity has no impact on the moisture content of the Form-I.

Formulation—

The sample of lenalidomide Form I API is encapsulated & compared with the REVLIMID capsules. The XRPD (X-ray powder diffractometry) of the encapsulated material of Lenadomide Form I is showing distinct peak at 7.786 2θ° value.

A distinct peak at 2θ° value of 7.786 that is characteristics peak of lenadomide Form I.

The polymorphic form of lenalidomide Form I is not changed even after encapsulation. The XRPD spectra of encapsulated material without lenadomide Form I API is also taken & major 2θ° values are deleted with XRD spectra of the Lenadomide capsules & compared the major peaks with REVILIMID capsules & found that peak are not matching.

The moisture content of the lenalidomide encapsulated material made with Form I is having 0.08% where as REVILIMID capsules is having 2.35%

The moisture content also shows that the polymorphic Form I is not changed to any of the hydrated form, and hence stable.

Bulk Density—

We observerd the following bulk density for three batches—
I. Batch No—0812/005
Untapped Density—0.278 g/ml
Tapped density—0.465 g/ml
II. Batch No—0812/006
Untapped Density—0.286 g/ml
Tapped density—0.481 g/ml
III. Batch No—0812/006
Untapped Density—0.286 g/ml
Tapped density—0.481 g/ml The following are the examples for the preparation of novel polymorphic Form-I and polymorphic Form-B are not limited to the scope of invention.

EXAMPLES

1. Preparation of Methyl 2-bromomethyl-3-nitro-benzoate

Into a 2.0 L 4-necked RB flask charged 100.0 g of methyl 2-methyl-3-nitro benzoate, 8.3 g of AIBN, 272.0 g of N-bromo succinimide and 1.5 L chlorobenzene under nitrogen atmosphere. Raised the temperature of the reaction mass to 90-95° C. Maintained the mass under maintenance temp. of 90-95° C. for about 6 hrs. The progress of the reaction is monitored by TLC. After TLC complies cool the mass to temperature 25 to 30° C. Filtered the mass and wash with methylene chloride. Washed the organic layer with DM water in two portions. Washed the organic layer with saturated aqueous sodium bicarbonate solution. Washed the organic layer with saturated sodium chloride solution. Dried the organic layer over sodium sulphate and filter. Distilled off the solvent completely under vacuum. Weight of crude oil is 120.0 g. To the above crude oil charged 600.0 ml of n-hexane. Stirred at temp. of 25-30° C. for 1 hr. Cooled the reaction mass temperature to 0-5° C. and maintain for 20-30 minutes Filtered the material and wash with 100 mL of Hexane. Weight of the wet material is 110.0 g. Dried the wet compound at 40-50° C. till constant weight is obtained.

Dry weight of the compound—100.0 g

1H NMR Spectra: δ values –4.00 (s, OCH3), 5.15 (s, C H2), 7.52-7.56 (t, Ar—H), 7.95-7.97 (d, Ar—H), 8.10-8.11 (d, Ar—H).

13C NMR Spectra: δ values –22.69 (CH2Br), 53.02 (O CH3), 127.77 (Ar—C), 129.08 (Ar—C), 132.3 (Ar—C), 1327.57 (Ar—C), 134.66 (Ar—C), 150.50 (Ar—C), 165.80 (C=O), 2. Preparation of 3-(4-nitro-1-oxo-1,3 dihydro-isoindol-2-yl)-piperidine-2,6-dione Into a 2.0 L dried 4 necked round bottom flask equipped with a condenser, an addition funnel and nitrogen gas bubbler under stirring, charged 50.0 g of methyl 2-bromomethyl-3-nitro-benzoate, 29.2 g of racemic 3-amino-piperidine-2,6-dione and 835.0 ml of DMF. Charged triethyl amine to the reaction mass at 25-35° C. in about 30-45 min. Raise the mass temperature to 95-100° C. Maintained the reaction mass at 95-100° C. for 6-6½ hrs under nitrogen atmosphere. The progress of the reaction is monitored by TLC. Poured the reaction mass slowly into 2.6 L of DM water at 25-35° C. under stirring in about 30-45 min. Maintained the reaction mass at 25-35° C. for 60-90 min under stirring. Filtered the material under vacuum, wash the wet cake with 215.0 ml of DM water, suck died the material. Dried the wet material in a oven at 60-65° C. for 4-5 hours. Weight of the dry material is—30.0 g.

3. Preparation of Lenalidomide Technical Grade Material

Into a 5.0 L 4 necked RB flask, charged 100.0 g of 3-(4-nitro-1-oxo-1,3 dihydro-isoindol-2-yl)-piperidine-2,6-dione, 10.0 g of 10% Pd/C and 3200 ml of DMF under nitrogen atmosphere. Stirred the mass and raise the reaction mass temperature to 60-65° C. Started the hydrogen gas bubbling into reaction mass at temperature 60-65° C. for 6 hours. The progress of the reaction is monitored by TLC. Cooled the mass to temperature 25 to 30° C. Filtered the catalyst Pd/C under plant vacuum in the presence of nitrogen atmosphere and wash with dimethylformamide; wet Pd/C is transferred into a polythene bag for recovery. Distilled off the above organic layer solvent completely under vacuum below 60° C. Charged ethyl acetate 800 ml (lot-I) to the mass and stirred for 60 min. Filtered the solid and wash with 200 mL of ethyl acetate (Lot-II). Dried the above wet material in a oven at temperature 65-75° C. for 120-180 min. Dried Weight of the compound is 78.0 g.

4. Purification of Lenalidomide to Get Form-B Material

Into a 1.0 L 4-necked round bottom flask, charged 20 g of Lenalidomide crude, and DM water 600 ml (Lot-I). Maintained stirring at temperature 25-35° C. for 5-10 min. Added Conc. HCl to the mass at 25-35° C. (pH of the mass is to be adjusted to 1-1.5) Maintained the mass at temperature 25-35° C. for 10-15 min. After clear solution formation is observed, charged carbon to the mass. Maintained the mass at temperature 25-35° C. for 10-15 min. Filtered the mass on hyflow bed under plant vacuum and wash with DM water. Transferred the above filtrate into a 1.0 L 4-necked round bottom flask, added ammonia solution to the filtrate and adjust the pH of the mass to 8-9. Maintained the mass at temperature 25-35° C. for 60-90 min. Filtered the mass under plant vacuum and washed with 10 ml of DM water, suck dried.

Dry Weight: 18.0 g.

Dried the wet material in a drier at temp 60-70° C. for 1.5 to 2.0 hrs under vacuum. The sample is analysed for moisture content, IR spectra, DSC, and Powder XRD.

The results are exactly matching with that of the values reported in the patent application US 2005/0096351 for polymorphic Form-B.

5. Purification of Lenalidomide to Get Form-I Material

Into 500 mL 4-neck round bottom flask, charge the above dry material (of the example 4) and IPA (200.0 ml). Raised the reaction mass temperature to 80° C. Maintained the mass at temperature 80-85° C. for 90-120 min. Started the distillation of IPA using downward distillation apparatus [Till MC decrease in the mass and sample IR matches with STD anhydrous sample]. Cooled the mass to temperature 25 to 30° C. Maintained the mass at temperature 25-35° C. for 60-90 min. Filtered the mass under plant vacuum, washed the wet cake with 10 ml of IPA and suck dried for 10 min. Dried the material at temperature 65-75° C. for 2-3 hrs. Dried Weight of the compound is—14.5 g. Dried sample is analysed for moisture content, IR spectra, TGA, DSC, and Powder XRD.

Powder XRD: 2 θ° Value 7.793, a distinct single peak. Also significant peaks are observed at 2θ Values 10.175, 11.269, 14.327, 15.772, 16.277, 17.646, 20.099, 20.508, 23.728, 24.098, 25.230, 25.987, 28.320, 32.595, DSC Thermograph: Peak maxima –266.64° C.

TGA Thermograph: Weight loss between 25° C. and 225° C. is 0.13%

IR Spectra: 3409.0, 3345.0, 3092.2, 1706.5, 1674.0, 1605.7, 1341.3, 1242.6, 1209.5, 882.0, 745.1 cm$^{-1}$

The invention claimed is:

1. A capsule comprising an anhydrous crystalline form of lenalidomide, which anhydrous crystalline form of lenalidomide is characterized by a distinct single peak in its powder XRD pattern at 7.786±0.2°2θ, and further peaks at 10.175±0.2°2θ and 11.269±0.2°2θ, wherein the peak at 10.175±0.2°2θ has substantially the same intensity as the peak at 11.269±0.2°2θ.

2. The capsule of claim 1, wherein the peaks at 10.175±0.2°2θ and 11.269±0.2°2θ each have an intensity of about 41% to about 47% of the intensity of the peak at 7.793±0.2°2θ.

3. A capsule comprising an anhydrous crystalline form of lenalidomide, wherein no single impurity level exceeds 0.10%.

4. The capsule of claim 3, wherein the anhydrous crystalline form of lenalidomide has a purity of more than 99.90%.

5. A process for producing a capsule of claim 1, comprising
   a) encapsulating an anhydrous crystalline form of lenalidomide, wherein said anhydrous crystalline form of lenalidomide is obtained following a drying step, and said drying step is carried out at a temperature of no more than 110° C.

6. The process of claim 5, wherein said anhydrous crystalline form of lenalidomide is characterized by a distinct single peak in its powder XRD pattern at 7.793 7.786±0.2°2θ, and further significant peaks at 10.175±0.2°2θ and 11.269±0.2°2θ.

7. The process of claim 5, wherein no single impurity level in the anhydrous crystalline form of lenalidomide exceeds 0.10%.

8. The process of claim 7, wherein the anhydrous crystalline form of lenalidomide has a purity of more than 99.90%.

* * * * *